US012779163B2

(12) United States Patent
Wang et al.

(10) Patent No.: US 12,779,163 B2
(45) Date of Patent: Nov. 3, 2026

(54) VENTILATION AND NOISE REDUCTION HOUSING AND ASSEMBLY, VENTILATION AND MOISTURE RETENTION APPARATUS, BREATHING MASK ASSEMBLY, AND BREATHING SUPPORT DEVICE

(71) Applicant: BMC (TIANJIN) MEDICAL CO., LTD., Tianjin (CN)

(72) Inventors: Yajie Wang, Tianjin (CN); Mingzhao Zhou, Tianjin (CN); Zhi Zhuang, Tianjin (CN); Yuanxiang Liu, Tianjin (CN); Guohui Ma, Tianjin (CN)

(73) Assignee: BMC (TIANJIN) MEDICAL CO., LTD., Tianjin (CN)

( * ) Notice: Subject to any disclaimer, the term of this patent is extended or adjusted under 35 U.S.C. 154(b) by 487 days.

(21) Appl. No.: 18/286,768

(22) PCT Filed: Apr. 12, 2022

(86) PCT No.: PCT/CN2022/086380

§ 371 (c)(1),
(2) Date: Oct. 13, 2023

(87) PCT Pub. No.: WO2022/218309

PCT Pub. Date: Oct. 20, 2022

(65) Prior Publication Data

US 2024/0189533 A1 Jun. 13, 2024

(30) Foreign Application Priority Data

Apr. 13, 2021 (CN) ......................... 202120745619.0

(51) Int. Cl.
*A61M 16/10* (2006.01)
*A61M 16/06* (2006.01)
*A61M 16/08* (2006.01)

(52) U.S. Cl.
CPC ........ *A61M 16/1045* (2013.01); *A61M 16/06* (2013.01); *A61M 16/0816* (2013.01);
(Continued)

(58) Field of Classification Search
CPC .............. A61M 16/1045; A61M 16/06; A61M 16/0816; A61M 16/0875; A61M 2205/42; A61M 2205/75; A61M 2202/0225
See application file for complete search history.

(56) References Cited

U.S. PATENT DOCUMENTS

2015/0126927 A1 5/2015 Flickinger
2018/0236200 A1 8/2018 Goldspink et al.
(Continued)

FOREIGN PATENT DOCUMENTS

CN 2834265 Y 11/2006
CN 104415442 A 3/2015
(Continued)

*Primary Examiner* — Timothy A Stanis
*Assistant Examiner* — Matthew R Moon
(74) *Attorney, Agent, or Firm* — Bayramoglu Law Offices LLC

(57) ABSTRACT

A ventilation and noise reduction housing and assembly, a ventilation and moisture retention apparatus, a breathing mask assembly and a breathing support device are provided. The ventilation and noise reduction housing includes a respiratory passage segment, one end thereof is a ventilation and noise reduction housing connection end, and the other end thereof is a respiratory tube communication end. The wall of the respiratory passage segment includes a mounting wall segment, that is provided with exhaust vents and a supporting protrusion structure protruding from the outer surface of the mounting wall segment, the supporting protrusion structure is used for supporting a ventilation and noise reduction core of a ventilation and noise reduction unit provided on the mounting wall segment, such that a venti- (Continued)

lation gap is at least partially maintained between the ventilation and noise reduction core and the outer surface of the mounting wall segment.

12 Claims, 10 Drawing Sheets

(52) U.S. Cl.
CPC ..... *A61M 16/0875* (2013.01); *A61M 2205/42* (2013.01); *A61M 2205/75* (2013.01)

(56) References Cited

U.S. PATENT DOCUMENTS

| | | | | |
|---|---|---|---|---|
| 2019/0209804 | A1* | 7/2019 | Dantanarayana | A61M 16/208 |
| 2019/0351173 | A1 | 11/2019 | Dantanarayana et al. | |
| 2022/0088336 | A1* | 3/2022 | Zhou | A61M 16/0622 |
| 2022/0134039 | A1* | 5/2022 | Hartono | A61M 16/0616 128/206.24 |

FOREIGN PATENT DOCUMENTS

| | | | |
|---|---|---|---|
| CN | 204208153 | U | 3/2015 |
| CN | 205323045 | U | 6/2016 |
| CN | 107212804 | A | 9/2017 |
| CN | 110975096 | A | 4/2020 |
| CN | 111493407 | A | 8/2020 |
| CN | 112089943 | A | 12/2020 |
| CN | 215024377 | U | 12/2021 |
| JP | H08332239 | A | 12/1996 |
| JP | 2019528921 | A | 10/2019 |
| WO | 2020111951 | A1 | 6/2020 |
| WO | 2020208523 | A1 | 10/2020 |

* cited by examiner

VENTILATION AND NOISE REDUCTION HOUSING AND ASSEMBLY, VENTILATION AND MOISTURE RETENTION APPARATUS, BREATHING MASK ASSEMBLY, AND BREATHING SUPPORT DEVICE

CROSS REFERENCE TO THE RELATED APPLICATIONS

This application is the national phase entry of International Application No. PCT/CN2022/086380, filed on Apr. 12, 2022, which is based upon and claims priority to Chinese Patent Application No. 202120745619.0, filed on Apr. 13, 2021, the entire contents of which are incorporated herein by reference.

TECHNICAL FIELD

The present disclosure relates to the technical field of medical instruments, in particular to a ventilation and noise reduction housing, a ventilation and noise reduction assembly, a ventilation and moisture retention apparatus, a breathing mask assembly, and a breathing support device.

BACKGROUND

At present, a mask respiratory system includes a ventilator, a respiratory tube and a breathing mask. The breathing mask includes a breathing chamber that can receive the nose or nose and mouth of a user, and then is secured to the user's face by a headband to form a sealed breathing chamber. Breathable gas generated by the ventilator can be delivered into the sealed breathing chamber through the respiratory tube, thereby performing respiratory treatment on the user. Further, in order to facilitate exhaust of the exhaled gas from the user, the breathing mask is typically provided with a gas vent so that the exhaled gas can be exhausted through the vent. Exhaled exhaust gas flushes the sidewalls of the vent to generate noise while passing through the vent.

In view of this, a layer of filter media is arranged next to the vent outside the vent, so that the exhaust gas discharged from the vent can only be discharged through the filter media. The filter media has a slowing effect on the exhaled exhaust gas, thereby effectively reducing such noise. However, at the same time, a new risk is introduced. Due to the filtering effect of the filter media, i.e. when it is used for a long time and is not cleaned as required, dust will accumulate at the vent, so that a flow value of the vent will be reduced. If the dust is not cleaned in time, the vent will be blocked, increasing the use risk, so that the treatment cannot achieve the expected effect.

Moreover, in use, such respiratory treatment generally takes a relatively long time, e.g., users generally need to wear the breathing mask throughout the day and night. When the air temperature is low and the air is dry, wearing such breathing mask for a long time will reduce the wearing comfort. To this end, the breathing machine is generally provided with a heating-humidification device such as a water tank or humidifier. When the gas passes through the water tank or humidifier, it will carry a portion of moisture to provide heated and humidified breathable gas to the user. However, typically, the ventilator is relatively big and difficult to be carried.

In view of this, solutions of the present disclosure are proposed.

SUMMARY

It is an object of the present disclosure to provide a ventilation and noise reduction housing capable of improving hygiene while reducing noise to improve a therapeutic effect.

In view of this, the present disclosure provides a ventilation and noise reduction housing, including a respiratory passage segment, one end of the respiratory passage segment being a ventilation-noise reduction housing connection end, the other end of the respiratory passage segment being a respiratory tube communication end; a wall of the respiratory passage segment includes a ventilation-noise reduction unit mounting wall segment; the ventilation-noise reduction unit mounting wall segment is provided with exhaust vents and a supporting protrusion structure protruding from an outer surface of the ventilation-noise reduction unit mounting wall segment, and the supporting protrusion structure is configured to support a ventilation and noise reduction core of a ventilation and noise reduction unit disposed on the ventilation-noise reduction unit mounting wall segment, so that a ventilation gap is at least partially maintained between the ventilation and noise reduction core and the outer surface of the ventilation-noise reduction unit mounting wall segment.

Further, the supporting protrusion structure is arranged close to the exhaust vents.

Further, the ventilation-noise reduction unit mounting wall segment includes an end face wall that extends outward in a radial direction, and the exhaust vents and the supporting protrusion structure are formed on the end face wall.

Further, the supporting protrusion structure includes an inclined surface between an upper surface and a front end surface of an outer end, in the radial direction, of the supporting protrusion structure.

In an embodiment, the supporting protrusion structure includes a plurality of radially extending convex ribs that are spaced in a circumferential direction, and the exhaust vents are spaced in the circumferential direction, and arranged between adjacent radially extending convex ribs.

Optionally, in an embodiment, the exhaust vents are spaced in the circumferential direction, and the supporting protrusion structure includes a circumferential protrusion located outside the exhaust vents in the radial direction.

Optionally, in an embodiment, the supporting protrusion structure includes a plurality of radially extending convex ribs that are spaced in the circumferential direction, and a plurality of protrusion groups that are spaced in the circumferential direction, the exhaust vents are spaced in the circumferential direction and arranged between adjacent radially extending convex ribs; the plurality of protrusion groups are located outside the exhaust vents in the radial direction, one of the protrusion groups is arranged between the adjacent radially extending convex ribs, and each of the protrusion groups includes a plurality of protrusions spaced in the circumferential direction.

Further, the supporting protrusion structure includes a plurality of rib segments in the circumferential direction, and a plurality of radially extending convex ribs that are spaced in the circumferential direction; the exhaust vents are spaced in the circumferential direction and arranged between adjacent radially extending convex ribs, one of the rib segments in the circumferential direction is arranged between adjacent radially extending convex ribs, and the rib segments in the circumferential direction are located outside the exhaust vents in the radial direction.

Further, the present application provides a ventilation and noise reduction assembly including a ventilation and noise reduction unit and any ventilation and noise reduction housing described above. The ventilation and noise reduction unit includes the ventilation and noise reduction core and a shell formed with a ventilation opening, the shell is connected to the ventilation-noise reduction unit mounting wall segment, the ventilation and noise reduction core is provided between the shell and the ventilation-noise reduction unit mounting wall segment, and is supported by the supporting protrusion structure, the ventilation gap is at least partially maintained between the ventilation and noise reduction core and the outer surface of the ventilation-noise reduction unit mounting wall segment, and the exhaust vents communicate with the ventilation opening through the ventilation and noise reduction core and the ventilation gap.

Further, the present application provides a ventilation and moisture retention apparatus including a ventilation and moisture retention apparatus housing and any ventilation and noise reduction housing as described above. The ventilation and moisture retention apparatus housing is connected to the ventilation and noise reduction housing connection end. The ventilation and moisture retention apparatus housing includes a breathing mask communication end, and the ventilation and moisture retention apparatus includes a respiratory passage between the breathing mask communication end and the respiratory tube communication end, and the respiratory passage includes the respiratory passage segment; the respiratory passage includes a ventilation and moisture retention unit receiving segment located between the breathing mask communication end and the respiratory tube communication end. The ventilation and moisture retention unit receiving segment is configured to receive the ventilation and moisture retention unit for allowing inhaled gas to pass through and hindering moisture and heat in the exhaled gas to pass through; the ventilation-noise reduction unit mounting wall segment is located between the ventilation and moisture retention unit receiving segment and the respiratory tube communication end.

Further, the ventilation and moisture retention unit includes the ventilation and noise reduction unit including the ventilation and noise reduction core and a shell formed with a ventilation opening. The shell is connected to the ventilation-noise reduction unit mounting wall segment, the ventilation and noise reduction core is provided between the housing and the ventilation and noise reduction unit mounting wall segment, and is supported by the supporting protrusion structure, a ventilation gap is at least partially maintained between the ventilation and noise reduction core and the outer surface of the ventilation-noise reduction unit mounting wall segment, and the exhaust vents communicate with the ventilation opening through the ventilation and noise reduction core and the ventilation gap.

Further, the ventilation and moisture retention apparatus includes a ventilation and moisture retention unit provided in the ventilation and moisture retention unit receiving segment.

Further, the ventilation and moisture retention unit includes an internal airway and an annular outer air cleft provided outside the internal airway. A ventilation and moisture retention core is provided inside the internal airway, the ventilation and moisture retention core is configured to allow inhaled gas to pass through and hinder moisture and heat in the exhaled gas to pass through. At least at an end portion of the ventilation and moisture retention unit facing the respiratory tube communication end, an annular outer sidewall of the outer air cleft extends axially beyond an annular inner sidewall of the outer air cleft, and one end of the annular inner sidewall includes an incoming air deflection surface for deflecting a portion of the axially flowing breathing gas toward the outer air cleft.

Further, the present application provides a breathing mask assembly including a breathing mask and the ventilation and noise reduction assembly described above. the breathing mask includes a mask body having a breathing cavity, the respiratory passage segment being in communication with the breathing cavity; or the breathing mask assembly includes a breathing mask and any of the ventilation and moisture retention apparatuses described above, and the breathing mask includes a mask body having a breathing cavity, the breathing mask communication end communicating with the breathing cavity.

Further, the present application provides a breathing support device including a ventilator, a respiratory tube, and the breathing mask assembly described above, the ventilator communicating with the respiratory tube communication end through the respiratory tube.

DESCRIPTION OF REFERENCE NUMERALS

1—respiratory passage segment, 2—ventilation and noise reduction housing connection end, 3—respiratory tube communication end, 4—ventilation-noise reduction unit mounting wall segment, 5—exhaust vent, 6—ventilation and noise reduction unit, 7—ventilation and noise reduction core, 8—ventilation gap, 9—end face wall, 10—radially extending convex rib, 11—protrusion group, 12—circumferential protrusion, 13—circumferential convex rib segment, 14—ventilation and noise reduction housing, 15—shell, 16—ventilation opening, 17—ventilation and moisture retention apparatus, 18—ventilation and moisture retention apparatus housing, 19—breathing mask communication end, 20—respiratory passage, 21—ventilation and moisture retention unit receiving segment, 22—ventilation and moisture retention unit, 23—ventilation and noise reduction assembly, 24—mask body, 25—internal airway, 26—external air cleft, 27—ventilation and moisture retention core, 28—connection sleeve, 29—inclined surface, 30—annular outer sidewall, 31—annular inner sidewall, 32—incoming air deflection surface.

DETAILED DESCRIPTION OF THE EMBODIMENTS

It should be noted that, embodiments and features in the embodiments of the present disclosure may be combined with each other without conflict. The present disclosure will be described in detail below with reference to the accompanying drawings in conjunction with embodiments.

Figure 1:
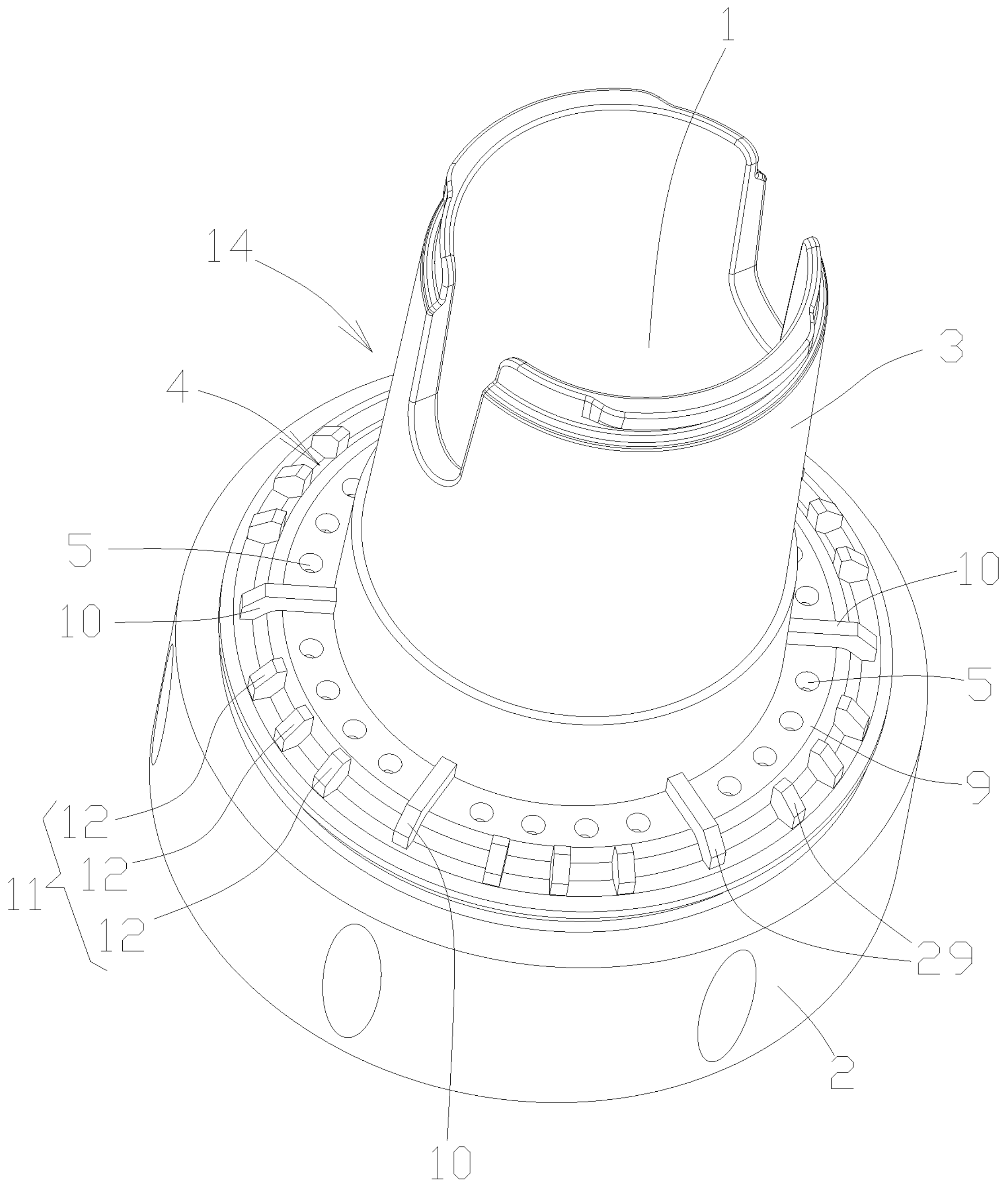
FIG. 1 is a schematic structural diagram of a first ventilation and noise reduction housing according to an embodiment of the present disclosure.
Figure 2:
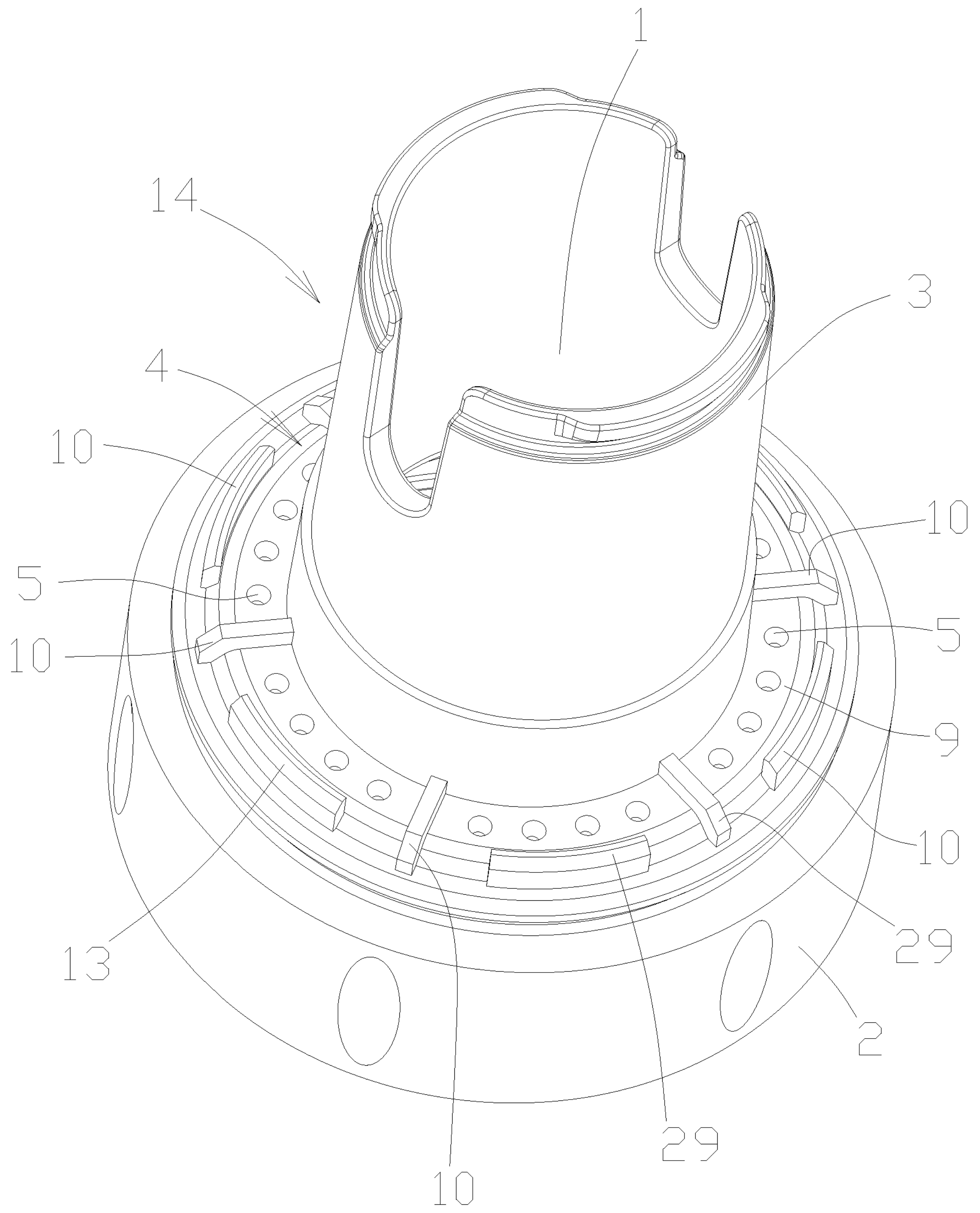
FIG. 2 is a schematic structural diagram of a second ventilation and noise reduction housing according to an embodiment of the present disclosure.

With reference to FIGS. 1 and 2, the present disclosure provides a ventilation and noise reduction housing 14, including: a respiratory passage segment 1, one end of the respiratory passage segment 1 being a ventilation and noise reduction housing connection end 2, and the other end thereof being a respiratory tube communication end 3. The ventilation and noise reduction housing connection end 2 may be connected to a ventilation and moisture retention apparatus housing 18 described below, or may be connected to other breathing tube components. The wall of the respiratory passage segment 1 includes a ventilation-noise reduction unit mounting wall segment 4, on which is provided with exhaust vents 5 and a supporting protrusion structure protruding from an outer surface of the ventilation-noise reduction unit mounting wall segment 4. The supporting protrusion structure is configured to support a ventilation and noise reduction core 7 of a ventilation and noise reduction unit 6 provided on the ventilation-noise reduction unit mounting wall segment 4, such that a ventilation gap 8 is at least partially maintained between the ventilation and noise reduction core 7 and the outer surface of the ventilation-noise reduction unit mounting wall segment 4.

In this technical solution, the ventilation-noise reduction unit mounting wall segment 4 is provided with exhaust vents 5 and the supporting protrusion structure protruding from the outer surface of the ventilation-noise reduction unit mounting wall segment 4; the supporting protrusion structure is configured to support the ventilation and noise reduction core 7 of the ventilation and noise reduction unit 6 provided on the ventilation-noise reduction unit mounting wall segment 4, such that a ventilation gap 8 is at least partially maintained between the ventilation and noise reduction core 7 and the outer surface of the ventilation-noise reduction unit mounting wall segment 4. Therefore, in the practical use of the ventilation and noise reduction housing 14, the ventilation and noise reduction unit 6 can be provided on the ventilation-noise reduction unit mounting wall segment 4, and the supporting protrusion structure supports the ventilation and noise reduction core 7 so that the ventilation gap 8 is at least partially maintained between the ventilation and noise reduction core 7 and the outer surface of the wall segment 4. When the exhaled exhaust gas is discharged from the exhaust vents 5, due to the ventilation gap 8, the exhaled exhaust gas will be discharged to the outside of the ventilation and noise reduction unit 6 through the ventilation gap 8 and the ventilation and noise reduction core 7, and the flow of the exhaled exhaust gas can be indicated by arrows in FIG. 4. Since the exhaled exhaust gas is retarded by the ventilation and noise reduction core 7, the noise generated by flushing the exhaust vents 5 by the exhaled exhaust gas are reduced, and the mute effect is improved. Moreover, a small portion of impurities, such as dust, carried in the exhaled exhaust gas will accumulate on the ventilation and noise reduction core 7, and most of the impurities will smoothly pass through the ventilation gap 8 along with the exhaled exhaust gas to be discharged to the outside of the ventilation and noise reduction unit 6 or accumulated at a position away from the exhaust vent 5, so that the exhaust vent 5 will not be blocked, thereby reducing the use risk of the user and improving the hygiene to improve the therapeutic effect.

The number of the exhaust vents 5 may be one, or may be more. A plurality of exhaust vents 5 may be arranged in a circumferential direction on only a segment of the circumferential wall, for example, a half of the circumferential wall, of the ventilation-noise reduction unit mounting wall segment 4, or may be arranged on a circle of the circumferential wall of the ventilation-noise reduction unit mounting wall segment 4.

In the ventilation and noise reduction housing 14, the supporting protrusion structure may be arranged at any position of the outer surface of the ventilation-noise reduction unit mounting wall segment 4 as long as it can support the ventilation and noise reduction core 7 of the ventilation and noise reduction unit 6 provided on the ventilation-noise reduction unit mounting wall segment 4 such that the ventilation gap 8 is at least partially maintained between the ventilation and noise reduction core 7 and the outer surface of the ventilation-noise reduction unit mounting wall segment 4. For example, the supporting protrusion structure may be provided at a position away from the exhaust vents 5. Alternatively, the supporting protrusion structure is arranged close to the exhaust vents 5, so that, for the ventilation and noise reduction core 7 made of a softer material, the supporting protrusion structure adjacent to the exhaust vent 5 can more easily support the ventilation and noise reduction core 7, thereby preventing the ventilation and noise reduction core 7 from covering all the exhaust vents 5. For example, when there are multiple exhaust vents 5, the ventilation and noise reduction core 7 can be prevented from blocking some of the exhaust vents 5.

Figure 3:
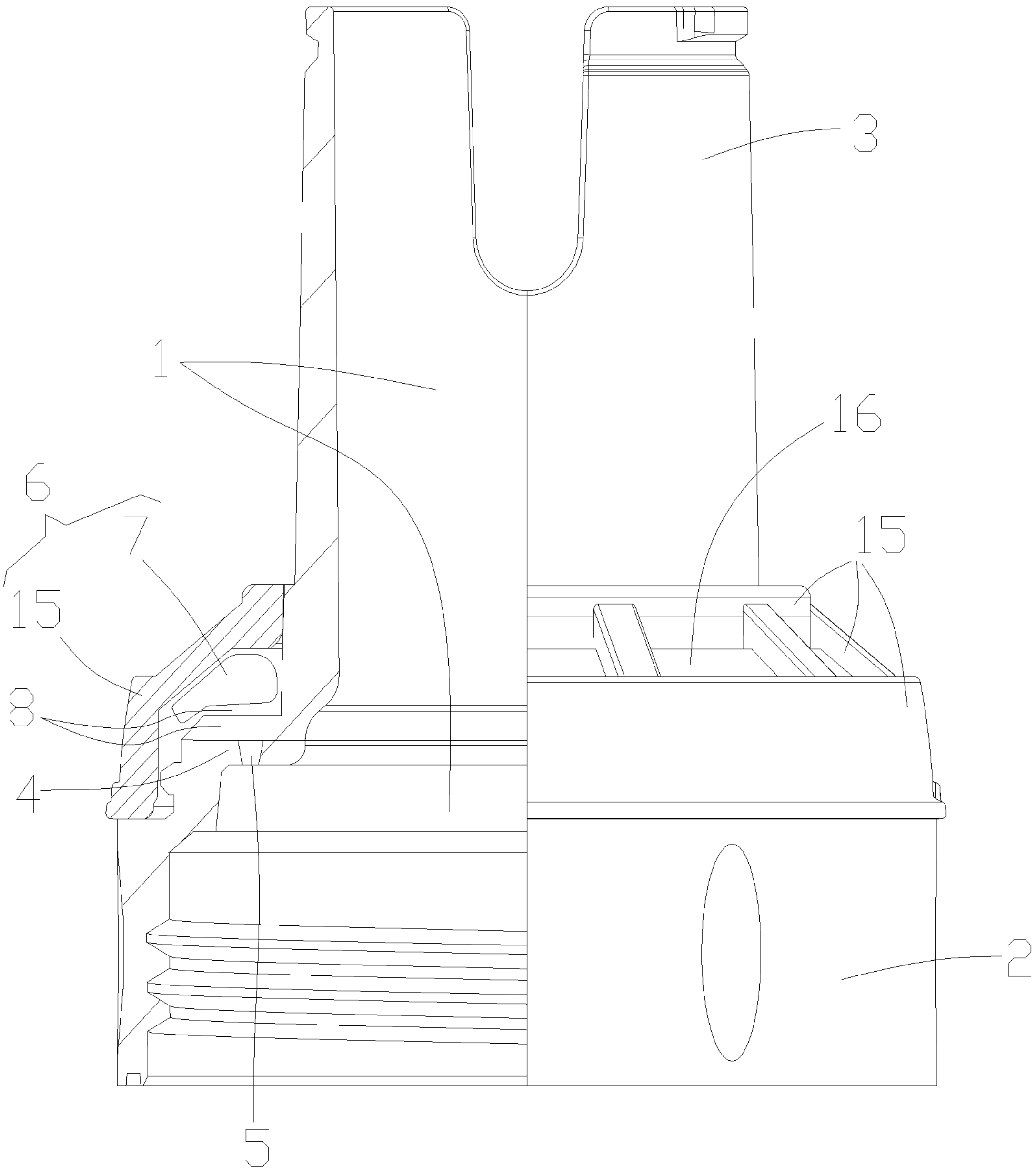
FIG. 3 is a schematic half-sectional view of a ventilation and noise reduction assembly according to an embodiment of the present disclosure.
Figure 4:
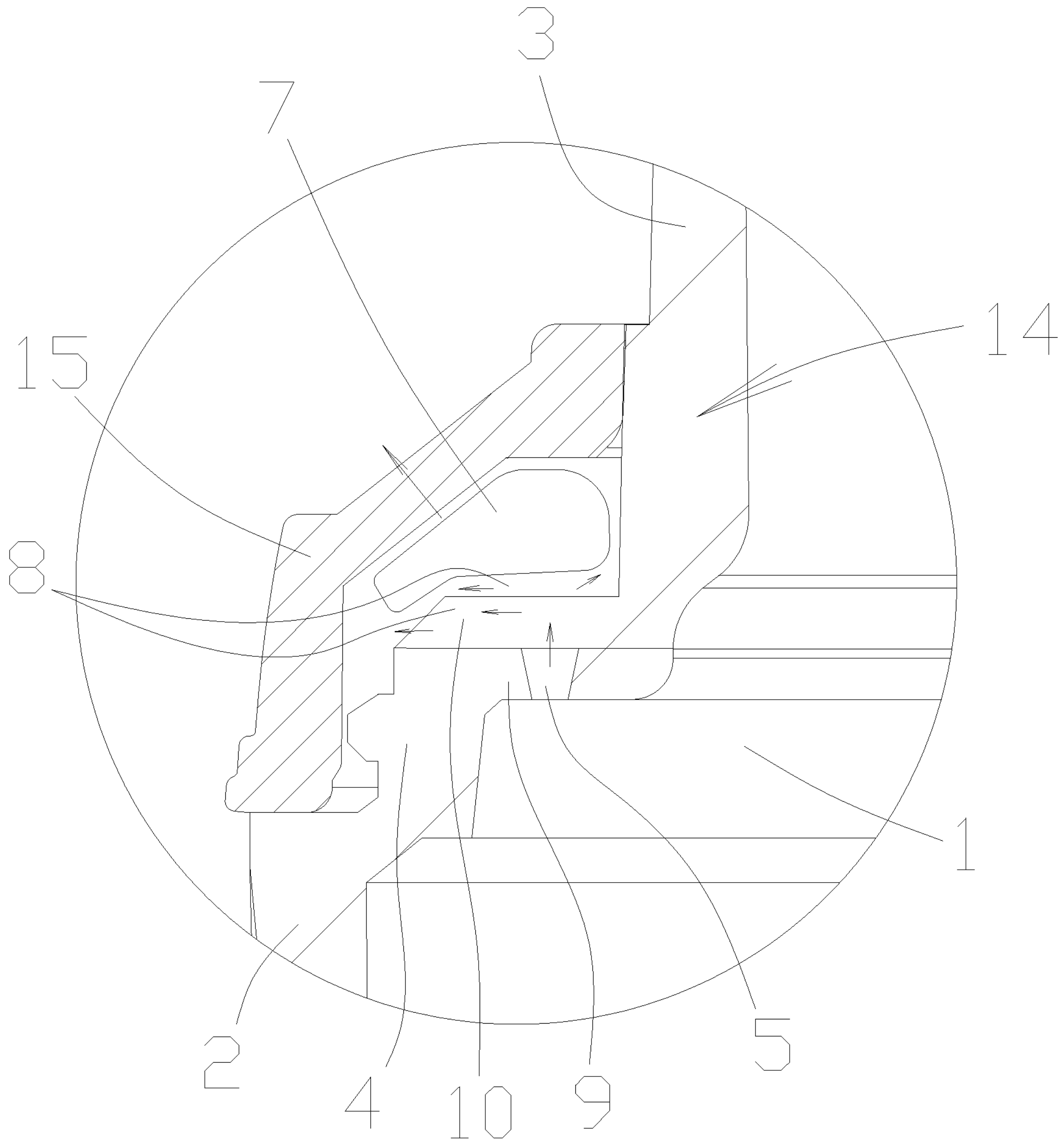
FIG. 4 is an enlarged schematic diagram of partial structures of FIG. 3.

In addition, in the ventilation and noise reduction housing 14, the ventilation-noise reduction unit mounting wall segment 4 may have various shapes, as long as it is formed with the exhaust vents 5 and the supporting protrusion structure so that the ventilation and noise reduction unit 6 can be mounted. For example, in one structure form, the ventilation-noise reduction unit mounting wall segment 4 includes an axial wall extending in an axial direction, on which exhaust vents are formed and from which the supporting protrusion structure extends, and the ventilation and noise reduction unit 6 may be mounted on the outer surface of the axial wall. Alternatively, referring to FIG. 1 to FIG. 4, the ventilation-noise reduction unit mounting wall segment 4 includes an end face wall 9 extending outward in the radial direction, on which the exhaust vents 5 and the supporting protrusion structure are formed such that, due to the end face wall 9 extending outward in the radial direction, the exhaled exhaust gas is more readily discharged from the exhaust vents 5 in the axial direction as it flows along the respiratory passage segment 1. Referring to FIGS. 3 and 4, the end face wall 9 may provide a mounting step that extends outward in the radial direction to the ventilation and noise reduction core 7, thereby improving the reliability of the ventilation and noise reduction core 7 provided on the mounting step. Alternatively, the ventilation-noise reduction unit mounting wall segment 4 includes an inclined wall that inclined outward in the axial direction, and the exhaust vents 5 and the supporting protrusion structures are formed on the end face wall 9.

In addition, referring to FIGS. 1 and 2, an inclined surface 29 is formed between the upper surface and the front end surface of the radial outer end of the supporting protrusion structure, that is, the inclined surface 29 is formed by cutting a portion of the radial outer end of the supporting protrusion structure between the upper surface and the front end surface. The portion of the space formed by cutting the radial outer end can be used to receive the ventilation and noise reduction core 7, thereby increasing the receiving space of the ventilation and noise reduction core 7. Thus, referring to FIGS. 3 and 4, when the ventilation and noise reduction core 7 is supported by the supporting protrusion structure, a part of the ventilation and noise reduction core 7 is bent to be received in the receiving space, or a part of the ventilation and noise reduction core 7 itself is bent to be received in the receiving space.

Further, in the ventilation and noise reduction housing 14, the supporting protrusion structure may have various shapes as long as the supporting protrusion structure can support the ventilation and noise reduction core 7 so that the ventilation gap 8 is at least partially maintained between the ventilation and noise reduction core 7 and the outer surface of the ventilation-noise reduction unit mounting wall segment 4. For example, in a first shape of the supporting protrusion structure, the supporting protrusion structure may include a first ring convex plate and a second ring convex plate. The first ring convex plate and the second ring convex plate may be spaced in the axial direction, or the first ring convex plate is spaced outside the second ring convex plate in the radial direction. The exhaust vents 5 are located between the first ring convex plate and the second ring convex plate, the ventilation and noise reduction core 7 may be supported by the first ring convex plate and the second ring convex plate so as to at least partially maintain the ventilation gap 8 with the outer surface of the ventilation-noise reduction unit mounting wall segment 4. The first ring convex plate and the second ring convex plate each is formed with a ventilation notch. Thus, a part of the exhaled exhaust gas discharged from the exhaust vents 5 can be discharged from the ventilation and noise reduction core 7, and another part of the exhaled exhaust gas flows into the ventilation gap 8 from the ventilation notch. The first and second ring convex plates may be provided on the aforementioned axial wall, the end face wall 9 or the inclined wall inclining outward in the axial direction.

As another example, in a second shape of the supporting protrusion structure, with reference to FIGS. 1 and 2, the supporting protrusion structure includes a plurality of radially extending convex ribs 10 that are spaced in a circumferential direction, and the exhaust vents 5 are spaced in the circumferential direction and are arranged between adjacent radially extending convex ribs 10. In this way, the ventilation and noise reduction core 7 is supported by the plurality of radially extending convex ribs 10 so that the ventilation gap 8 is at least partially maintained between the outer surface of the ventilation-noise reduction unit mounting wall segment 4 and the ventilation and noise reduction core 7. Further, the radially extending convex rib 10 can separate the exhaust vents 5 on both sides thereof, so that exhaled exhaust gas emerging from the plurality of exhaust vents 5 between the two radially extending convex ribs 10 passes through the ventilation gap 8 rapidly, which may carry away impurities carried in the exhaled exhaust gases more quickly to avoid accumulation at the exhaust vents 5.

The plurality of radially extending convex ribs 10 may be provided on the aforementioned axial wall, the end face wall 9 or the inclined wall inclined outward in the axial direction. The plurality of radially extending convex ribs 10 may be arranged close to the exhaust vents. The inclined surface 29 may be provided between the upper surface and the front end surface of the radially outer ends of each of the plurality of radially extending convex ribs 10.

As yet another example, in a third shape of the supporting protrusion structure, referring to FIG. 1, the plurality of exhaust vents 5 are spaced in the circumferential direction, the supporting protrusion structure includes a plurality of circumferentially spaced protrusions 12 that are located outside the exhaust vents 5 in the radial direction. In this way, the ventilation and noise reduction core 7 may be supported by the plurality of circumferential protrusions 12 so that the ventilation gap 8 is at least partially maintain between the ventilation and noise reduction core 7 and the outer surface of the ventilation-noise reduction unit mounting wall segment 4. The plurality of circumferentially spaced circumferential protrusions 12 may support and lift up the entire ventilation and noise reduction core 7 to increase the ventilation gap 8 to further prevent blocking the exhaust vents 5 and improve safety. The plurality of circumferential protrusions 12 may be provided on the end face wall 9 or the inclined wall inclined outward in the axial direction. The plurality of circumferential protrusions 12 may be arranged close to the exhaust vents. The inclined surface 29 may be provided between the upper surface and the front end surface of the radially outer end of each of the plurality of circumferential protrusions 12.

As another example, in a fourth form of the supporting protrusion structure, with reference to FIG. 1, the supporting protrusion structure includes a plurality of radially extending convex ribs 10 that are spaced in the circumferential direction, and a plurality of protrusion groups 11 that are spaced in the circumferential direction. The exhaust vents 5 are spaced in the circumferential direction, and are arranged between adjacent radially extending convex ribs 10. The plurality of protrusion groups 11 are located outside the exhaust vents 5 in the radial direction. One protrusion group 11 is arranged between adjacent radially extending convex ribs 10, and each protrusion group 11 includes a plurality of circumferentially spaced protrusions 12. In this way, the ventilation and noise reduction core 7 may be supported by the plurality of radially extending convex ribs 10 and the plurality of circumferentially spaced protrusions 12 to at least partially maintain the ventilation gap 8 with the outer surface of the ventilation-noise reduction unit mounting wall segment 4. Moreover, the radially extending convex rib 10 can separate the exhaust vents 5 on both sides thereof, so that exhaled exhaust gas emerging from the exhaust vents 5 between two radially extending convex ribs 10 passes through the ventilation gap 8 rapidly, which may carry away impurities carried in the exhaled exhaust gases more quickly to avoid accumulation at the exhaust vents 5. The plurality of circumferential protrusions 12 in the plurality of protrusion groups 11 spaced circumferentially may further support and lift up the entire ventilation and noise reduction core 7 to increase the ventilation gap 8, further avoiding blocking the exhaust vents 5 and improving safety.

As another example, in a fifth shape of the supporting protrusion structure, referring to FIG. 2, the supporting protrusion structures include a plurality of circumferential convex rib segments 13, and a plurality of radially extending convex ribs 10 that are spaced in the circumferential direction. Exhaust vents 5 are spaced circumferentially between adjacent radially extending convex ribs 10, and one circumferential convex rib segment 13 is arranged between adjacent radially extending convex ribs 10. The circumferential convex rib segment 13 is located outside the exhaust vents 5 in the radial direction, and the circumferential convex rib segment 13 is spaced from the radially extending convex ribs 10 at both circumferential ends thereof. In this way, the ventilation and noise reduction core 7 may be supported by the plurality of radially extending convex ribs 10 and the plurality of circumferential convex rib segments 13 to at least partially maintain the ventilation gap 8 with the outer surface of the ventilation-noise reduction unit mounting wall segment 4. Moreover, the radially extending convex rib 10 can separate the exhaust vents 5 on both sides thereof, so that exhaled exhaust gases emerging from the plurality of exhaust vents 5 between two radially extending convex ribs 10 to pass through the ventilation gap 8 rapidly, which may carry away impurities carried in the exhaled exhaust gases more quickly to avoid accumulation at the exhaust vents 5. Furthermore, the circumferential convex rib segment 13 can support and lift up the whole ventilation and noise reduction core 7 to increase the ventilation gap 8, thereby further avoiding blocking the exhaust vents 5 and improving the safety.

In addition, the ventilation and noise reduction housing 14 may be made of materials such as PP, PC, nylon or polycarbonate PC, preferably PC. The wall thickness of the ventilation and noise reduction housing 14 is 1 to 3 mm, preferably 1.5 mm. The internal dimension of the exhaust vent 5, for example the diameter, is 0.5 to 1.5 mm, preferably 0.8 mm. When there are multiple exhaust vents 5, the vent spacing between the exhaust vents 5 is 2 to 8 mm, preferably 4 mm. Further, the height of the radially extending convex rib 10, the circumferential protrusion 12 and the circumferential convex rib segment 13 may be 0.5 mm to 3.5 mm, preferably 1 mm, and the thickness of the radially extending convex rib 10, the circumferential protrusion 12 and the circumferential convex rib segment 13 may be 0.5 mm to 2 mm, preferably 1 mm.

In addition, the ventilation and noise reduction housing connection end 2 may have various structural forms as long as the ventilation and noise reduction housing 14 can be connected. For example, referring to FIG. 3, the ventilation and noise reduction housing connection end 2 is a connection barrel having a connection thread formed on an outer surface or an inner surface thereof.

Figure 8:
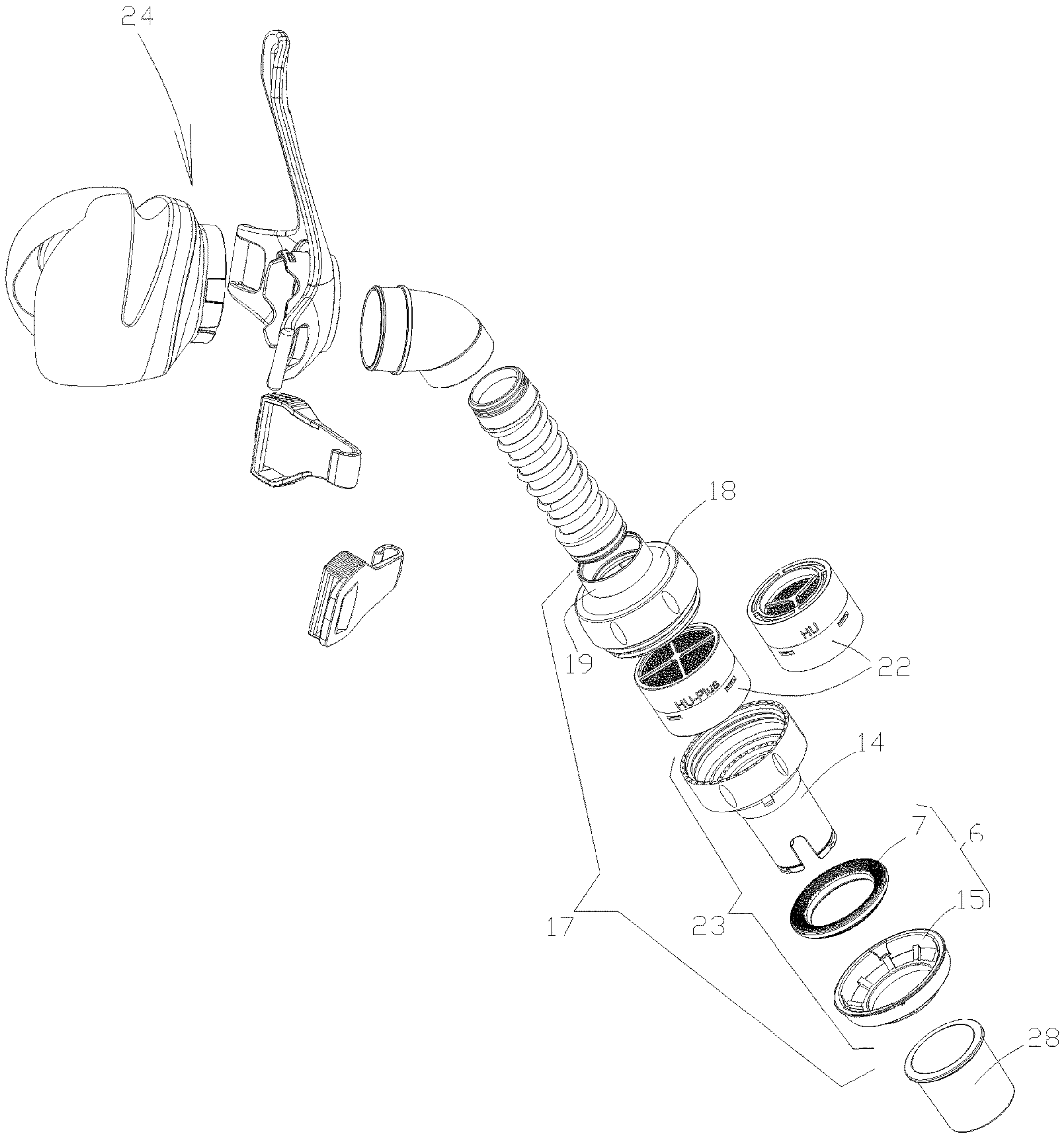
FIG. 8 is an exploded view of a breathing mask assembly according to an embodiment of the present disclosure.

Further, the present disclosure provides a ventilation and noise reduction assembly 23. Referring to FIGS. 3, 4 and 8, the ventilation and noise reduction assembly 23 includes a ventilation and noise reduction unit 6 and any of the ventilation and noise reduction housings 14 as described above. The ventilation and noise reduction unit 6 includes a ventilation and noise reduction core 7, and a shell 15 formed with a ventilation opening 16. The shell 15 is connected to the ventilation-noise reduction unit mounting wall segment 4, and the ventilation and noise reduction core 7 is disposed between the shell 15 and the ventilation-noise reduction unit mounting wall segment 4, and is supported by the supporting protrusion structure. In this way, the ventilation gap 8 is maintained at least partially between the ventilation and noise reduction core 7 and the outer surface of the ventilation-noise reduction unit mounting wall segment 4, and the exhaust vent 5 communicates with the ventilation opening 16 through the ventilation and noise reduction core 7 and the ventilation gap 8.

As described above, in practical use of the ventilation and noise reduction assembly 23, the supporting protrusion structure supports the ventilation and noise reduction core 7 so that the ventilation gap 8 is at least partially maintained between the ventilation and noise reduction core 7 and the outer surface of the ventilation-noise reduction unit mounting wall segment 4. When the exhaled exhaust gas is discharged from the exhaust vents 5, the exhaled exhaust gas will be discharged to the outside of the ventilation and noise reduction unit 6 through the ventilation gap 8 and the ventilation and noise reduction core 7 due to the ventilation gap 8, and the flow of the exhaled exhaust gas can be indicated by the arrow in FIG. 4. Since the exhaled exhaust gas is retarded by the ventilation and noise reduction core 7, the noise generated by flushing the exhaust vents 5 with the exhaled exhaust gas is reduced and the mute effect is improved. Moreover, a small portion of impurities, such as dust, carried in the exhaled exhaust gas may accumulate on the ventilation and noise reduction core 7, and a large portion of impurities may smoothly pass through the ventilation gap 8 along with the exhaled exhaust gas to be discharged to the outside of the ventilation and noise reduction unit 6, or accumulate at a position away from the exhaust vents 5. Therefore, the exhaust vents 5 will not be blocked, thereby reducing the use risk of the user and improving the hygiene to improve the therapeutic effect.

The ventilation and noise reduction core 7 may be made of filter media or a silk mass. Moreover, the shape of the ventilation and noise reduction core 7 may be selected accordingly according to the arrangement shape of the exhaust vents 5. For example, for the exhaust vents 5 shown in FIG. 1 and FIG. 2, the ventilation and noise reduction core 7 may be a ring shown in FIG. 8.

Moreover, the shell 15 may have various configurations. For example, the shell 15 may be an annular net that may be clamped on the passage segments. For example, referring to FIG. 8, the shell 15 includes an outer ring and an inner ring. The inner ring is arranged within the outer ring with a ring spacing, and the outer ring is connected to the inner ring through a plurality of circumferentially spaced connection strips arranged within the ring spacing. The plurality of connection strips divide the ring spacing into ventilation openings 16, meanwhile, the connection strips can restrict the filter media assembled inside, so that the filter media assembled inside is stable. Thus, as shown in FIGS. 8 and 9, in one embodiment, the respiratory tube connection end may pass through the inner ring, and the outer ring is connected to the respiratory passage segment, so as to position the annular filter media to cover the exhaust vents 5 annularly arranged to further mitigate exhaust noise.

Figure 5:
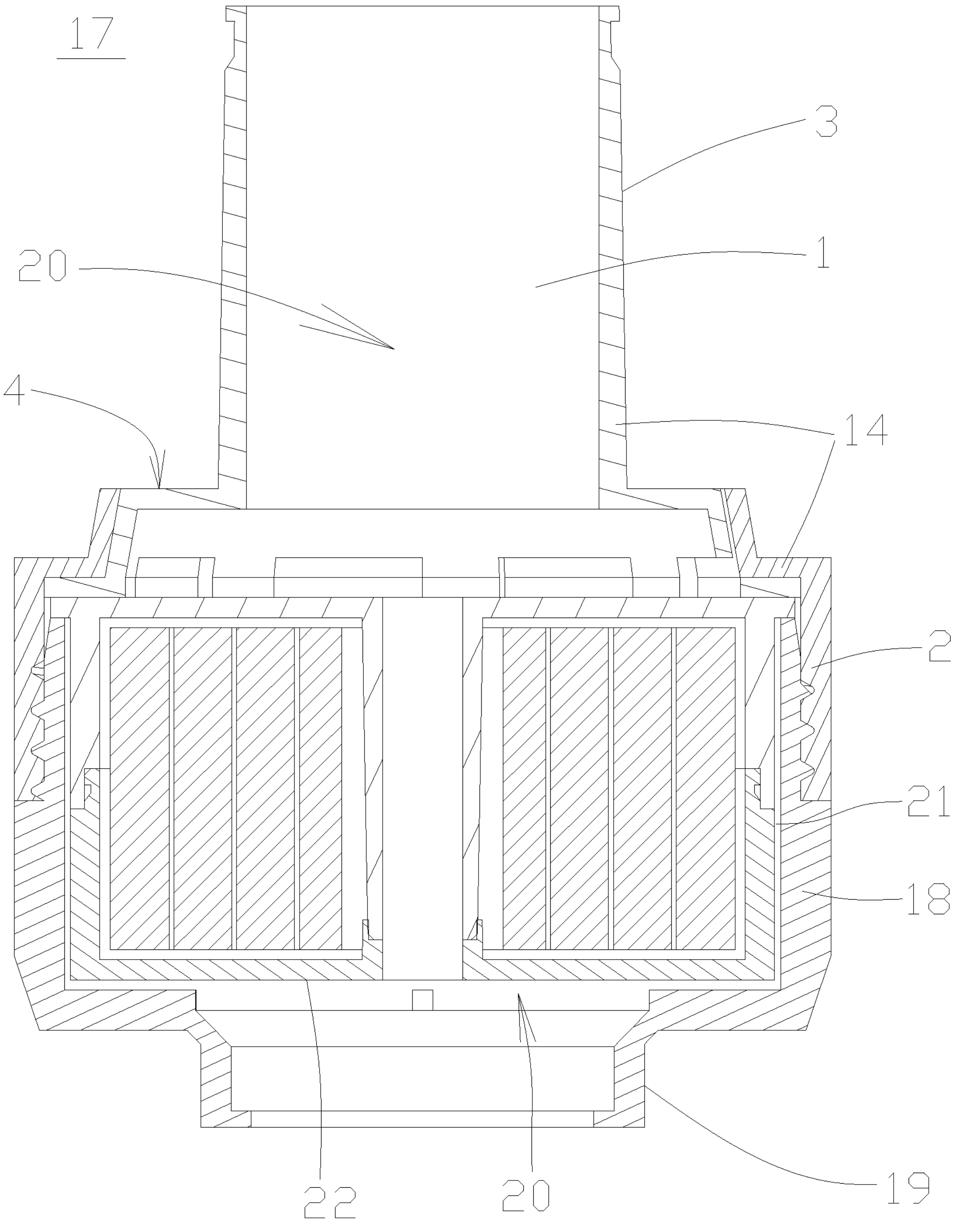
FIG. 5 is a schematic cross-sectional view of a ventilation and moisture retention apparatus according to an embodiment of the present disclosure, where a ventilation and moisture retention unit and a third ventilation and noise reduction housing provided by the present application are shown.
Figure 9:
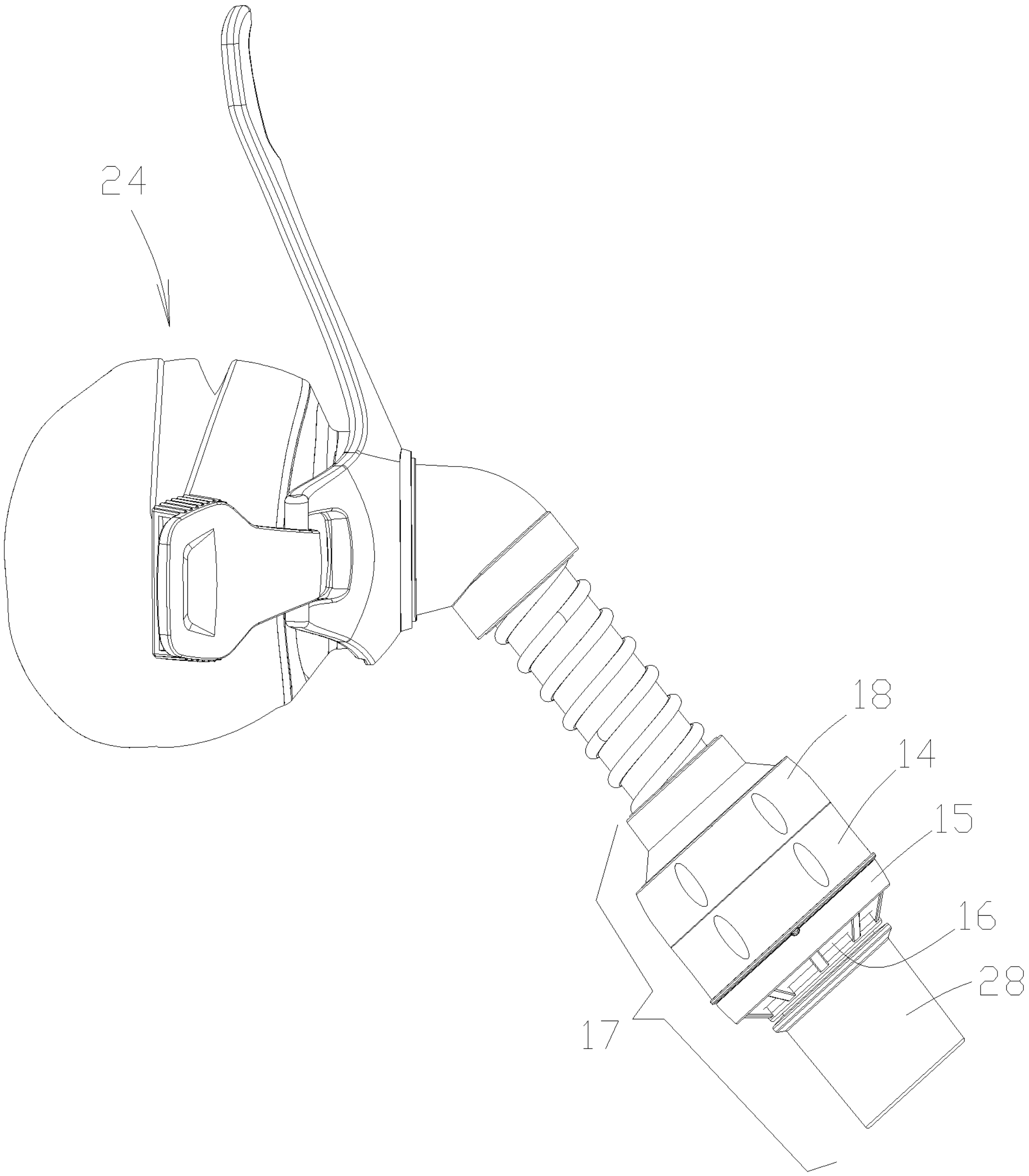
FIG. 9 is an assembling diagram of the breathing mask assembly of FIG. 8.

Further, the present disclosure provides a ventilation and moisture retention apparatus, and with reference to FIGS. 5, 8 and 9, the ventilation and moisture retention apparatus 17 includes a ventilation and moisture retention apparatus housing 18 and any ventilation and noise reducing housing 14 as described above. The ventilation and moisture retention apparatus housing 18 is connected to the ventilation and noise reduction housing connection end 2. The ventilation and moisture retention apparatus housing 18 includes a breathing mask communication end 19. The ventilation and moisture retention apparatus 17 includes a breathing passage 20 located between the breathing mask communication end 19 and the respiratory tube communication end 3. The breathing passage 20 includes: a respiratory passage segment 1; a ventilation and moisture retention unit receiving segment 21 located between the breathing mask communication end 19 and the respiratory tube communication end 3.

The ventilation and moisture retention unit receiving segment 21 is configured to receive and arrange a ventilation and moisture retention unit 22 that allows inhaled gas to pass through and retards moisture and heat in the exhaled gas to pass through. The ventilation-noise reduction unit mounting wall segment 4 is located between the ventilation and moisture retention unit receiving segment 21 and the respiratory tube communication end 3.

In the technical solution, the ventilation and moisture retention unit receiving segment 21 is configured to receive and arrange the ventilation and moisture retention unit 22 that allows the breathing gas to pass through and retards moisture and heat in the exhaled gas to pass through, and the ventilation-noise reduction unit mounting wall segment 4 is located between the ventilation and moisture retention unit receiving segment 21 and the respiratory tube communication end 3. In this way, in use, the ventilation and moisture retention unit 22 that allows the breathing gas to pass through and capable of retard moisture and heat in the exhaled gas to pass though may be provided within the ventilation and moisture retention unit receiving segment 21. The ventilation and moisture retention unit 22 can be used for allowing the breathing gas to pass through and retarding the moisture and heat in the exhaled gas to pass through, and the breathing mask communication end is communicated with the breathing mask, so that the exhaled gas (exhaust gas) of a wearer can pass through the ventilation and moisture retention unit and be exhausted from the vents. In this case, since the moisture and heat in the exhaled air are retarded by the ventilation and moisture retention unit, the humidity in the passage segment between the breathing mask communication end and the ventilation and moisture retention unit will increase, and the moisture may condense in the ventilation and moisture retention unit 22 so that the internal humidity of the ventilation and moisture retention unit also increases. Moreover, the heat contained in the exhaled gas increases the temperature of the passage segment between the breathing mask communication end and the ventilation and moisture retention unit, and increases the temperature of the ventilation and moisture retention unit. As a result, when breathable gas supplied to the wearer passes through the ventilation and moisture retention unit and the passage segment between the breathing mask communication end and the ventilation and moisture retention unit, due to the action of increased humidity and increased temperature, moist and warm breathable gas can be supplied to the wearer by the ventilation and moisture retention apparatus. Therefore, the comfortable sensation of wearing the breathing mask is improved. Moreover, the ventilation and moisture retention apparatus can be communicated with the breathing mask and the respiratory tube, and since the breathing mask and the respiratory tube are light and convenient, the ventilation and moisture retention apparatus is small in volume and can be carried with flexibility and it is possible to provide moist and warm breathing gas to the wearer of the breathing mask in a flexible and convenient way. Of course, if it is desired, the ventilation and moisture retention unit receiving segment may be used to receive and hold ventilation and moisture retention units of at least two different specifications, so that a desired ventilation and moisture retention unit can be flexibly and conveniently replaced. Moreover, as stated above, since the supporting protrusion structure supports the ventilation and noise reduction core so that the ventilation gap is at least partially maintained between the ventilation and noise reduction core and the outer surface of the wall segment for mounting a ventilation and noise reduction unit, when the exhaled exhaust gas is discharged from the exhaust vents, due to the ventilation gap, the exhaled exhaust gas will pass through the ventilation gap and the ventilation and noise reduction core and be discharged to the outside from the ventilation opening, and due to the mitigation effect of the ventilation and noise reduction core on the exhaled exhaust gas, the noise generated by flushing on the exhaust vents with the exhaled exhaust gas are reduced and the mute effect is improved. Moreover, a small portion of impurities, such as dust, carried in the exhaled exhaust gas may accumulate on the ventilation and noise reduction core, and most of the impurities will smoothly pass through the ventilation gap along with the exhaled exhaust gas to be discharged to the outside, or accumulated at a position away from the exhaust vents. Therefore, the exhaust vents will not be blocked, thereby reducing the use risk of the user and improving the hygiene to improve the therapeutic effect.

In addition, with reference to FIGS. 8 and 9, the ventilation and moisture retention apparatus includes the ventilation and noise reduction unit 6. The ventilation and noise reduction unit 6 includes the ventilation and noise reduction core 7, and the shell 15 formed with the ventilation opening 16. The shell 15 is connected to the ventilation-noise reduction unit mounting wall segment 4. The ventilation and noise reduction core 7 is arranged between the shell 15 and the ventilation-noise reduction unit mounting wall segment 4, and is supported by the supporting protrusion structure, the ventilation gap 8 is at least partially maintained between the ventilation and noise reduction core 7 and the outer surface of the ventilation-noise reduction unit mounting wall segment 4, and exhaust vents 5 communicate with the ventilation opening 16 via the ventilation and noise reduction core 7 and the ventilation gap 8. In this way, as described above, the ventilation and moisture retention apparatus can conveniently provide moist and warm breathing gas to the wearer of the breathing mask while reducing exhaust noise and improving hygiene.

In addition, the ventilation and moisture retention unit 22 may be not included in the ventilation and moisture retention apparatus, and in use, it may be fitted into the ventilation and moisture retention unit receiving segment 21. Alternatively, referring to an embodiment shown in FIG. 5, and another embodiment shown in FIGS. 8 and 9, the ventilation and moisture retention apparatus includes a ventilation and moisture retention unit 22 provided in the ventilation and moisture retention unit receiving segment 21, that is, for a ventilation and moisture retention apparatus as a separate product, the ventilation and moisture retention unit receiving segment 21 is equipped with the ventilation and moisture retention unit 22.

Figure 6:
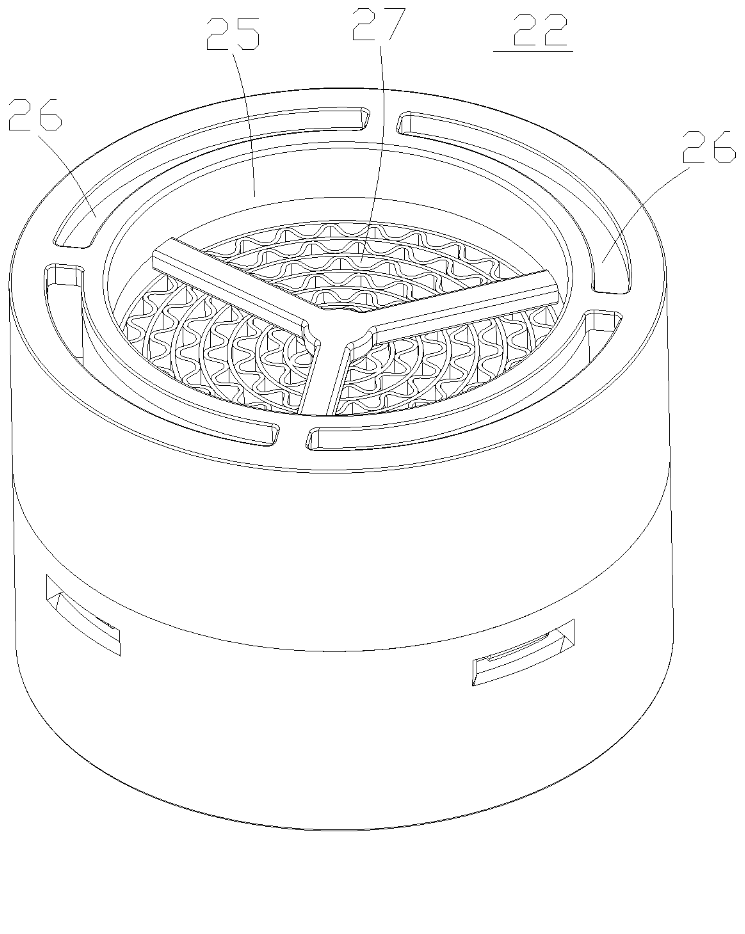
FIG. 6 is a perspective diagram illustrating another ventilation and moisture retention unit used in a ventilation and moisture retention apparatus according to an embodiment of the present disclosure.
Figure 7:
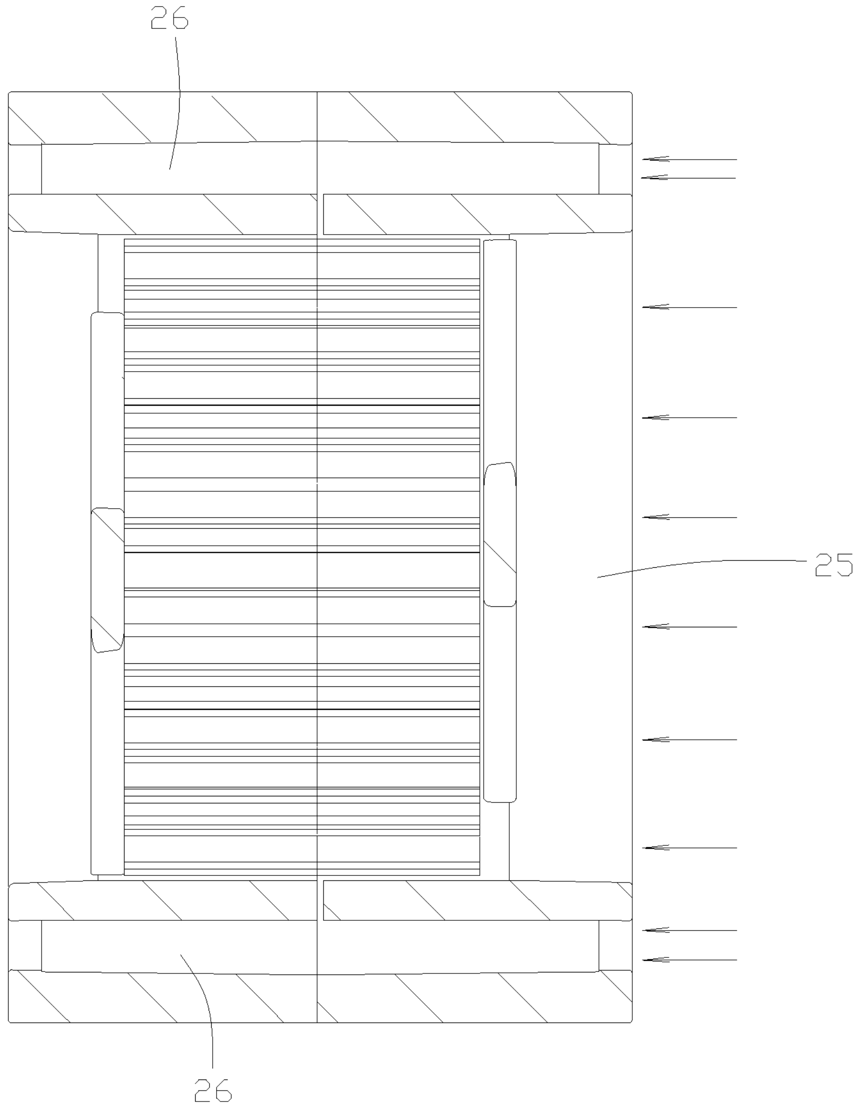
FIG. 7 is a schematic cross-sectional view of FIG. 6.

Further, the ventilation and moisture retention unit 22 may have various forms. For example, FIG. 5 shows one type of ventilation and moisture retention unit 22, and FIG. 8 shows two ventilation and moisture retention units 22 of different specifications. For example, referring to the ventilation and moisture retention unit 22 shown in FIGS. 6 and 7, the ventilation and moisture retention unit 22 includes an internal airway 25 and an annular outer air cleft 26. A ventilation and moisture retention core 27 is arranged in the internal airway 25. The ventilation and moisture retention core 27 allows the breathing gas to pass, and can retard moisture and heat in the exhaled gas to pass through. Thus, with reference to FIG. 7, the exhaled exhaust gas may directly rush the end plane of the ventilation and moisture retention core 27, as indicated by the arrows in FIG. 7, and may disperse into the outer air cleft 26. During breathing, as the inhaled airflow and the exhaled exhaust gas may encounter, which may further retard the exhaled exhaust gas to pass through the outer air cleft 26, thereby reducing the noise caused by rushing the outer air cleft 26 with the exhaled airflow. Compared with the supplied inhaled gas flow, the flow rate of the gas exhaled by the human body is relatively low, thus most of the exhaled exhaust gas will pass through the internal airway 25 under the effect of the relatively strong supplied inhaled gas flow, which also further increases the moisture and heat retention performance.

Figure 10:
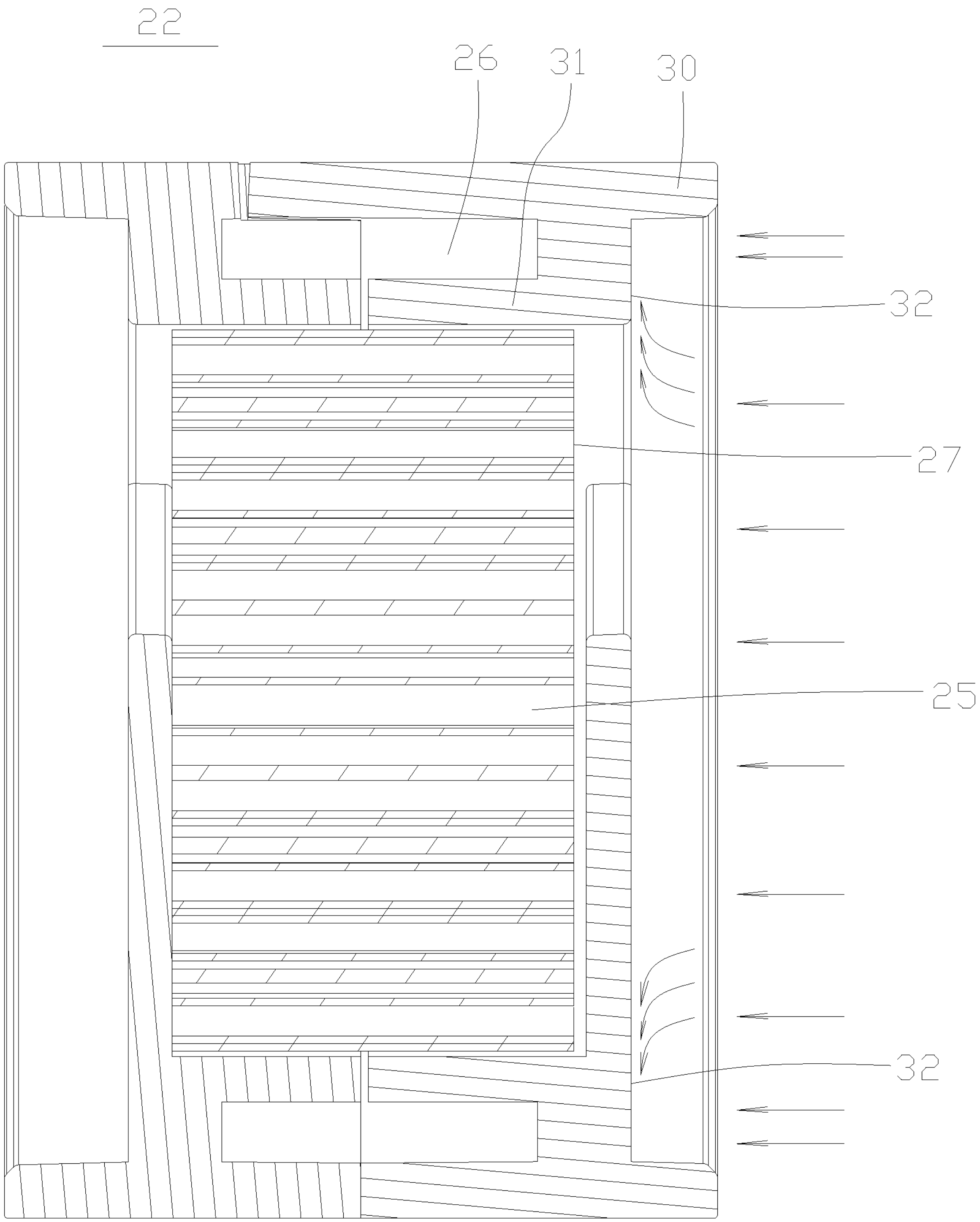
FIG. 10 is a schematic cross-sectional view of a ventilation and moisture retention unit of other structures used in a ventilation and moisture retention apparatus according to an embodiment of the present disclosure.

Further, referring to FIG. 10, in another alternative embodiment of the ventilation and moisture retention unit 22, the ventilation and moisture retention unit 22 includes an internal airway 25 and an annular outer air cleft 26 provided outside the internal airway 25. A ventilation and moisture retention core 27 is provided inside the internal airway 25. The ventilation and moisture retention core 27 is configured to allow the inhaled gas to pass and retard the moisture and heat in the exhaled gas to pass. At least at an end portion of the ventilation and moisture retention unit 22 facing the respiratory tube communication end 3, an annular outer sidewall 30 of the outer air cleft 26 extends axially beyond an annular inner sidewall 31 of the outer air cleft 26, and an end of the annular inner sidewall 31 includes an incoming air deflection surface 32 for deflecting a portion of the inhaled gas axially flowing toward the outer air cleft 26. As such, referring to FIG. 10, since the annular outer sidewall 30 of the outer air cleft 26 extends axially beyond the annular inner sidewall 31 of the outer air cleft 26, the axial length of the ventilation and moisture retention core 27 can be reduced in the internal airway 25. Since the resistance of the outer air cleft 26 is low and the air resistance of the internal airway 25 is greater, the flow rate of the outer air cleft 26 is fast and the flow rate of the internal airway 25 is slow, thereby causing a difference between the inner and outer pressures. As a result, most of the inhaled gas will pass through the outer air cleft 26, so that the resistance of the inhaled gas is significantly reduced, facilitating easier aspiration of the inhaled gas by the patient. Moreover, as shown by the curved arrows in FIG. 10, since the incoming air deflection surface 32 can deflect and guide a portion of the inhaled gas flowing in the axial direction toward the outer air cleft 26, and a portion of the gas is deflected again to reach the inner surface of the annular outer sidewall 31 to have an opposite impact with the intake air flow, which weakens the energy of the air flow, thereby reducing the noise caused by striking the housing of the ventilation and moisture retention unit 22 by the breathing gas flow. Compared with the inhaled airflow entering from the intake end, the flow rate of the exhaled air exhaled by the human body is relatively low, and under the effect of the relatively stronger airflow, most of the exhaled air will pass through the ventilation and moisture retention core 27 in the internal airway 25, which will also increase the moisture retention performance.

Moreover, the incoming air deflection surface 32 may be formed at one end of the annular inner sidewall 31 in various ways. For example, a portion of the end of the annular inner sidewall 31 shown in FIG. 7 may be cut away so that the end surface of the annular inner sidewall 31 shown in FIG. 7 serves as the incoming air deflection surface 32. Alternatively, an annular incoming air deflector may be provided at one end of the annular inner sidewall 31, and the plate surface of the incoming air deflector may serve as the incoming air deflection surface 32.

Further, the respiratory tube communication end 3 may be directly connected to the respiratory tube, or may be fitted with a connection sleeve 28 which may be connected to the respiratory tube.

Further, the present disclosure provides a breathing mask assembly. Referring to FIGS. 8 and 9, the breathing mask assembly includes a breathing mask and the ventilation and noise reduction assembly 23 described above. The breathing mask includes a mask body 24 having a breathing cavity, and the respiratory passage segment 1 communicates with the breathing cavity. For example, the respiratory passage segment 1 may be connected directly to the mask body 24, or may be connected to the mask body 24 by other conduits of the breathing mask assembly, such as a hose or the like. Thus, as described above, the quality of the breathing mask assembly is effectively improved.

Further, the present disclosure provides a breathing mask assembly. Referring to FIGS. 8 and 9, the breathing mask assembly includes a breathing mask and any ventilation and moisture retention apparatus 17 described above. The breathing mask includes a mask body 24 having a breathing cavity, and the breathing mask communication end 19 communicates with the breathing cavity. For example, the breathing mask communication end 1 may be connected directly to the mask body 24, or may be connected to the mask body 24 by other conduits of the breathing mask assembly, such as a hose or the like. Thus, as described above, the quality of the breathing mask assembly is effectively improved.

Finally, the present disclosure provides a breathing support device including a ventilator (not shown), a respiratory tube (not shown) and a breathing mask assembly as described above. The ventilator communicates with the respiratory tube communication end 3 through the respiratory tube. Thus, as described above, the quality of the breathing support device is effectively improved.

The preferred embodiments of the present disclosure have been described in detail above with reference to the accompanying drawings, but the present disclosure is not limited thereto. Many simple variations of the solution of the present disclosure are possible within the scope of the technical idea of the present disclosure. The particular features included are combined in any suitable manner. To avoid unnecessary repetitions, the present disclosure does not further describe various possible combinations. However, these simple modifications and combinations should also be regarded as the disclosure of the present disclosure and all fall within the scope of the present disclosure.

What is claimed is:

1. A ventilation and noise reduction housing, comprising a respiratory passage segment, a first end of the respiratory passage segment being a ventilation and noise reduction housing connection end, a second end of the respiratory passage segment being a respiratory tube communication end, wherein a wall of the respiratory passage segment comprises a ventilation-noise reduction unit mounting wall segment, the ventilation-noise reduction unit mounting wall segment is provided with exhaust vents and a supporting protrusion structure protruding from an outer surface of the ventilation-noise reduction unit mounting wall segment, and the supporting protrusion structure is configured to support a ventilation and noise reduction core of a ventilation and noise reduction unit disposed on the ventilation-noise reduction unit mounting wall segment, so that a ventilation gap is at least partially maintained between the ventilation and noise reduction core and the outer surface of the ventilation-noise reduction unit mounting wall segment;

wherein the supporting protrusion structure comprises a plurality of radially extending convex ribs that are spaced in the circumferential direction, and a plurality of protrusion groups that are spaced in the circumferential direction, wherein the exhaust vents are spaced in the circumferential direction and arranged between adjacent radially extending convex ribs; the plurality of protrusion groups are located outside the exhaust vents in the radial direction, one of the protrusion groups is arranged between the adjacent radially extending convex ribs, and each of the protrusion groups comprises a plurality of protrusions spaced in the circumferential direction; or wherein the supporting protrusion structure comprises a plurality of convex rib segments in the circumferential direction, and a plurality of radially extending convex ribs that are spaced in the circumferential direction, wherein the exhaust vents are spaced in the circumferential direction and arranged between adjacent radially extending convex ribs, one of the convex rib segments in the circumferential direction is arranged between adjacent radially extending convex ribs, and the convex rib segments in the circumferential direction are located outside the exhaust vents in the radial direction.

2. The ventilation and noise reduction housing according to claim 1, wherein the supporting protrusion structure is arranged close to the exhaust vents.

3. The ventilation and noise reduction housing according to claim 1, wherein the ventilation-noise reduction unit mounting wall segment comprises an end face wall that extends outward in a radial direction, and the exhaust vents and the supporting protrusion structure are formed on the end face wall.

4. The ventilation and noise reduction housing according to claim 3, wherein the supporting protrusion structure comprises an inclined surface between an upper surface and a front end surface of an outer end, in the radial direction, of the supporting protrusion structure.

5. A ventilation and noise reduction assembly, comprising a ventilation and noise reduction unit and the ventilation and noise reduction housing according to claim 1, wherein the ventilation and noise reduction unit comprises the ventilation and noise reduction core, and a shell formed with a ventilation opening, the shell is connected to the ventilation-noise reduction unit mounting wall segment, the ventilation and noise reduction core is disposed between the shell and the ventilation-noise reduction unit mounting wall segment and is supported by the supporting protrusion structure, the ventilation gap is at least partially maintained between the ventilation and noise reduction core and the outer surface of the ventilation-noise reduction unit mounting wall segment, and the exhaust vents communicate with the ventilation opening through the ventilation and noise reduction core and the ventilation gap.

6. A breathing mask assembly, comprising a breathing mask and the ventilation and noise reduction assembly according to claim 5, wherein the breathing mask comprises a mask body having a breathing cavity, and the respiratory passage segment communicates with the breathing cavity.

7. A breathing support device, comprising a ventilator, a respiratory tube and the breathing mask assembly according to claim 6, wherein the ventilator communicates with the respiratory tube communication end via the respiratory tube.

8. A ventilation and moisture retention apparatus, wherein the ventilation and moisture retention apparatus comprises a ventilation and moisture retention apparatus housing and the ventilation and noise reducing housing according to claim 1, wherein the ventilation and moisture retention apparatus housing is connected to the ventilation and noise reduction housing connection end, and the ventilation and moisture retention apparatus housing comprises a breathing mask communication end, the ventilation and moisture retention apparatus comprises a respiratory passage located between the breathing mask communication end and the respiratory tube communication end, and the respiratory passage comprises the respiratory passage segment;

the respiratory passage comprises a ventilation and moisture retention unit receiving segment positioned between the breathing mask communication end and the respiratory tube communication end, and the ventilation and moisture retention unit receiving segment is configured to receive a ventilation and moisture retention unit for allowing inhaled gas to pass through and retarding moisture and heat in exhaled gas to pass through;

the ventilation-noise reduction unit mounting wall segment is located between the ventilation and moisture retention unit receiving segment and the respiratory tube communication end.

9. The ventilation and moisture retention apparatus according to claim 8, comprising a ventilation and noise reduction unit, wherein the ventilation and noise reduction unit comprises the ventilation and noise reduction core and a shell formed with a ventilation opening, the shell is connected to the ventilation and noise reduction unit mounting wall segment, the ventilation and noise reduction core is disposed between the shell and the ventilation and noise reduction unit mounting wall segment and is supported by the supporting protrusion structure, the ventilation gap is at least partially maintained between the ventilation and noise reduction core and the outer surface of the ventilation and noise reduction unit mounting wall segment, and the exhaust vents communicate with the ventilation opening through the ventilation and noise reduction core and the ventilation gap.

10. The ventilation and moisture retention apparatus according to claim 8, comprising a ventilation and moisture retention unit provided in the ventilation and moisture retention unit receiving segment.

11. The ventilation and moisture retention apparatus according to claim 10, wherein the ventilation and moisture retention unit comprises an internal airway and an annular outer air cleft provided outside the internal airway, wherein a ventilation and moisture retention core is provided inside the internal airway, the ventilation and moisture retention core is configured to allow inhaled gas to pass through and retard the moisture and heat in the exhaled gas to pass through, wherein at least at an end portion of the ventilation and moisture retention unit facing the respiratory tube communication end, an annular outer sidewall of the outer air cleft extends axially beyond an annular inner sidewall of the outer air cleft, and one end of the annular inner sidewall comprises an incoming air deflection surface for deflecting a portion of inhaled gas flowing in the axial direction toward the outer air cleft.

12. A breathing mask assembly, comprising a breathing mask and the ventilation and moisture retention apparatus according to claim 8, wherein the breathing mask comprises a mask body having a breathing cavity, and the breathing mask communication end communicates with the breathing cavity.

* * * * *